United States Patent [19]

Keating et al.

[11] Patent Number: 5,274,138
[45] Date of Patent: Dec. 28, 1993

[54] EPOXIDATION PROCESS FOR MANUFACTURE OF OLEFIN OXIDE AND ALCOHOL

[75] Inventors: Kenneth P. Keating, Georgetown; Edward T. Marquis; Mark A. Mueller, both of Austin, all of Tex.

[73] Assignee: Texaco Chemical Company, White Plains, N.Y.

[21] Appl. No.: 6,542

[22] Filed: Jan. 21, 1993

[51] Int. Cl.$^5$ .................. C07D 301/19; C07D 303/04
[52] U.S. Cl. ................................. 549/529; 568/909.8
[58] Field of Search .......................................... 549/529

[56] References Cited

U.S. PATENT DOCUMENTS

| | | | |
|---|---|---|---|
| 3,351,635 | 11/1967 | Kollar | 260/348.5 |
| 3,849,451 | 11/1974 | Stein et al. | 260/348.5 L |
| 4,455,283 | 6/1984 | Sweed | 423/53 |
| 4,598,057 | 7/1986 | Isaacs | 502/24 |
| 4,626,596 | 12/1986 | Marquis et al. | 556/57 |
| 4,650,886 | 3/1987 | Marquis et al. | 556/57 |
| 4,654,427 | 3/1987 | Marquis et al. | 556/57 |
| 4,703,027 | 10/1987 | Marquis et al. | 502/171 |
| 4,758,681 | 7/1988 | Marquis et al. | 556/57 |
| 4,891,437 | 1/1990 | Marquis et al. | 549/529 |
| 4,992,566 | 2/1991 | Marquis et al. | 549/529 |

FOREIGN PATENT DOCUMENTS

| | | | |
|---|---|---|---|
| 2300204 | 7/1973 | Fed. Rep. of Germany | 549/529 |
| 1298253 | 11/1972 | United Kingdom | |
| 1337296 | 11/1973 | United Kingdom | 549/529 |

*Primary Examiner*—Joseph E. Evans
*Attorney, Agent, or Firm*—James L. Bailey; Kenneth R. Priem; Douglas H. May

[57] ABSTRACT

An epoxidation reaction wherein: an olefin and an organic hydroperoxide, preferably, propylene and tertiary butyl hydroperoxide are reacted in a primary reaction zone in a liquid phase with an organic solvent, preferably tertiary butyl alcohol, in the presence of a soluble molybdenum catalyst at a ratio of propylene to tertiary butyl hydroperoxide of from about 0.9:1 to about 3:1, at a reaction temperature from about 100° C. to about 140° C. and a residence time sufficient to convert about 85 to 95% of the tertiary butyl hydroperoxide and form a primary epoxidation zone reaction product; fractionating, in a primary fractionation zone, the primary zone reaction product into a primary distillate fraction comprising unreacted propylene and propylene oxide and into a primary heavy liquid fraction, comprising molybdenum catalyst, unreacted tertiary butyl hydroperoxide, tertiary butyl alcohol and side reaction products; reacting, in a secondary epoxidation reaction zone, the primary heavy liquid fraction with propylene in the liquid phase, with substantially no back mixing, at a molar ratio of propylene to unreacted tertiary butyl hydroperoxide of about 5:1 to about 10:1, a reaction temperature of about 110° C. to about 140° C. and a residence time sufficient for conversion of substantially all the tertiary butyl hydroperoxide and production of a secondary reaction zone product; fractionating the secondary reaction zone product, in a secondary distillation zone, into a secondary distillate fraction comprising unreacted propylene, and propylene oxide, and into a secondary heavy liquid fraction comprising molybdenum catalyst, tertiary butyl alcohol, and side reaction products; recovering the secondary heavy liquid product for recovery and/or disposal of molybdenum; and fractional distillation of the first distillate fraction and the second distillate fraction for recovery of propylene, and propylene oxide product.

9 Claims, 1 Drawing Sheet

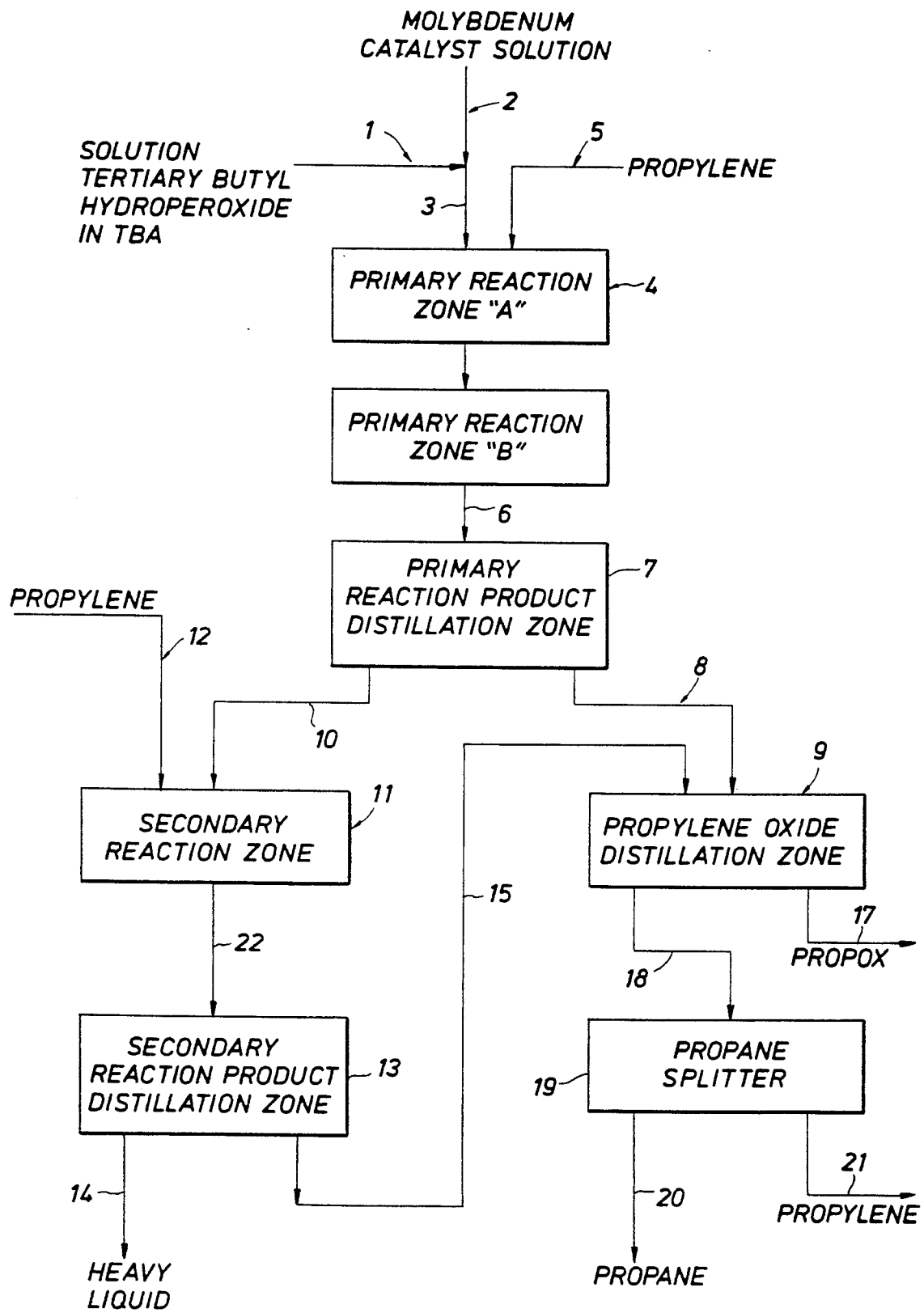

EPOXIDATION PROCESS FOR MANUFACTURE OF OLEFIN OXIDE AND ALCOHOL

BACKGROUND OF THE INVENTION

1. Field of the Invention

The present invention relates to the process for epoxidation of olefins with an organic hydroperoxide, in the liquid phase with an organic solvent, in the presence of a soluble epoxidation catalyst. More particularly, the present invention relates to an improved epoxidation process including: oxidation of an olefin with a hydroperoxide, typically propylene with tertiary butyl hydroperoxide, in a primary reaction zone in liquid phase with an organic solvent, typically tertiary butyl alcohol, under epoxidation conditions for conversion of about 85 to 95% of the tertiary butyl hydroperoxide and for production of a first epoxidation reaction product; fractionation of the primary epoxidation reaction product into a first distillate fraction comprising unreacted propylene and propylene oxide, and into a primary liquid fraction comprising molybdenum catalyst, unreacted tertiary butyl hydroperoxide, tertiary butyl alcohol, and side reaction products; reaction of the primary liquid fraction with propylene in a secondary epoxidation zone under epoxidation conditions for conversion of about 85 to about 95% of the tertiary butyl hydroperoxide charged in the first liquid fraction, and for production of a secondary epoxidation reaction product; fractionation of the secondary epoxidation reaction product into a second distillate fraction comprising unreacted propylene and propylene oxide and into a secondary liquid fraction comprising molybdenum catalyst, tertiary butyl alcohol, and side reaction products; and recovering propylene and propylene oxide product from the primary and secondary distillate fractions.

2. Description of Pertinent Art

The epoxidation reactions contemplated herein are epoxidation reactions of the type disclosed by Kollar, U.S. Pat. No. 3,351,653, as have been elaborated, for example, in Marquis, et al., U.S. Pat. No. 4,891,437, where a wide variety of olefins can be epoxidized using a wide variety of organic hydroperoxides in the presence of catalytic metallic compounds.

Processes for epoxidation of $C_3$–$C_{20}$ olefin hydrocarbons with an organic hydroperoxide in the presence of an epoxidation catalyst selected from compounds of molybdenum titanium, tungsten, vanadium and selenium to produce olefin oxide and an alcohol corresponding to the hydroperoxide are well known. Typically, commercial reactions employ propylene as olefin and tertiary butyl hydroperoxide as organic hydroperoxide. Products of these reactions, propylene oxide and tertiary butyl alcohol, are valuable intermediate chemicals for the manufacture of other products such as synthetic polymers and tertiary butyl ether.

In British Patent Specification No. 1,298,253, filed Jul. 14, 1970, a method is disclosed for the continuous epoxidation of propylene with tertiary butyl hydroperoxide in the presence of a molybdenum catalyst, which process comprises: reacting propylene in excess with tertiary butyl hydroperoxide in the presence of tertiary butyl alcohol solvent and molybdenum catalyst in a first epoxidation zone; fractionating effluent from the first reaction zone to yield an overhead fraction containing unreacted propylene, propylene oxide and tertiary butyl alcohol, and yield a bottoms fraction containing unconverted tertiary butyl hydroperoxide, the remainder of the tertiary butyl alcohol and molybdenum catalyst; separating the bottoms fraction into a recycle stream and a purge stream and recycling the recycle stream to said first epoxidation zone; reacting the purge stream in a second epoxidation zone with propylene; and recovering the propylene oxide product from each of said epoxidation zones. The British Specification claims as advantages for this process that consumption of catalysts is extremely low, tertiary butyl hydroperoxide conversion is high, and at the same time selectivity (i.e., moles of propylene oxide produced per mole of tertiary butyl hydroperoxide converted) is high, thus providing a high yield of propylene oxide based upon the amount of tertiary butyl hydroperoxide charged to the process. A review of the examples shows selectivity of tertiary butyl hydroperoxide conversion to propylene oxide is 57% without the second stage reaction of the present invention and 66% with the second stage reaction.

In British Specification 1,298,253, a large recycle stream containing catalyst and side reaction products is returned to the first epoxidation zone where it is brought into contact with the epoxidation reaction mixture, including propylene oxide as well as propylene and tertiary butyl hydroperoxide reactants. This recycle stream, in addition to containing molybdenum catalyst and unconverted tertiary butyl hydroperoxide, also contains side reaction products including low molecular weight ($C_1$–$C_4$) carboxylic acids. These carboxylic acids catalyze additional side reactions including propylene dimerization reactions and propylene oxide-tertiary butyl hydroperoxide esterification and etherification reaction the products of which reduce selectivity, and yield of desired product. The purge stream, which forms the charge stock to the second reactor in the disclosed process, must of necessity remove the side reaction products at a rate equivalent to the rate at which they are formed. Since the purge stream is, as disclosed in the specification, only 8 to 20% of the heavy liquid stream from the distillation zone, the recycle stream returns to the first reaction zone from 5 to 12 times the amount of side reaction products, including the low molecular weight acids, as are produced in the initial reaction.

Stein, et al, in U.S. Pat. No. 3,849,451, issued Nov. 19, 1974, discloses a process for a catalytic epoxidation of olefinically unsaturated compounds employing organic hydroperoxides as epoxidizing agents and employing catalysts comprised of metals such as vanadium, tungsten, molybdenum, titanium and selenium. In Stein, et al., an epoxidation reaction is carried out under autogenous pressure and at a reaction temperature sufficient to volatilize a portion of the liquid phase reaction medium, including a portion of the olefin oxide product. Preferably from $\frac{1}{8}$ to $\frac{1}{2}$ of the olefin oxide product and substantially none of the organic hydroperoxide is removed with the volatilized portion. Preferably, the reaction zone is partitioned into several compartments with a common overhead zone, or alternatively, several reactors in series are employed to prevent back mixing of epoxidation reaction product with reactants entering the process. In Stein, et al., the unreacted olefin and a portion ($\frac{1}{8}$ to $\frac{1}{2}$) of the olefin oxide product are vaporized and withdrawn from each compartment or from each series reactor. Olefin recovered from the withdrawn vapor is returned as reactant to each compartment or each series reactor. Stein, et al. recognizes that the olefin oxide product enters into side reactions catalyzed by the acidic side reaction products of the epoxidation reaction. However, in the process of Stein, et al., only a portion (⅛ to ½) of the olefin oxide is removed from each reactor compartment or reactor in series, leaving a substantial portion (½ to 2/3) of the olefin oxide in contact with the acidic compounds under conditions favorable for side reactions which consume olefin oxide.

Sweed, in U.S. Pat. No. 4,455,283, issued Jun. 19, 1984, discloses a process for epoxidizing olefin compounds with organic hydroperoxides in the presence of liquid solutions of dissolved molybdenum catalysts, and for recovery and recycle of the molybdenum catalyst values. In the description of the prior art, (column 2, lines 16-22) Sweed notes that distillation residue containing spent molybdenum catalyst, some alcohol, and acids as well as high boiling organic residues can be recycled directly to the epoxidation reaction zone, but direct recycle of the residue results in a build up within the system of impurities (e.g. acids) which are deleterious to subsequent epoxidation reactions.

Isaacs, in U.S. Pat. No. 4,598,057, issued Jul. 1, 1986, discloses a process for epoxidation of olefins with organic hydroperoxides in the presence of a molybdenum catalyst with subsequent recovery of molybdenum from a spent catalyst stream derived from the epoxidation reaction product. In the detailed description of the invention at column 4, lines 57-68, Isaacs states, "As indicated above, this heavy fraction cannot be recycled directly to the epoxidation zone in view of the fact that the impurities contained therein, and most notably the acid impurities, interfere with the epoxidation reaction. The deleterious effect of these acids is particularly pronounced in a continuous system due to a build up of the concentration of these materials when a direct recycle is employed. Furthermore, partial recycle of the stream to the epoxidation reaction, over a period of time, results in accumulation of residual materials associated with the catalyst which likewise is deleterious to the overall epoxidation reaction."

From the above references, it is seen that reactions for epoxidation of olefin using organic hydroperoxide in the presence of selected metal catalysts, such as molybdenum, are well known. Also, it is recognized that reactions catalyzed by acid side reaction products consume olefin oxide product and organic hydroperoxide reactant, thus reducing yield from the epoxidation reactions. Efforts, as disclosed in U.S. Pat. No. 3,849,451 and British Specification 1,298,253 discussed above, employing more than one reactor in the epoxidation process have been made to reduce the consumption of propylene oxide and organic hydroperoxide in unwanted side reactions. These efforts have not been completely successful. Either through recycle of acidic side reaction products to the main reactor, or through incomplete removal of olefin oxide from charge to a second reactor, the olefin oxide continued to remain in contact with acidic side reaction products. These acidic side reaction products catalyze reactions such as etherification and esterification reactions, which destroy the olefin oxide product and organic hydroperoxide. Consequently, improvements to the epoxidation process which will improve hydroperoxide conversion and increase product yields without increasing side reactions which consume olefin oxide and organic hydroperoxide, are desirable.

SUMMARY OF THE INVENTION

This invention is directed to a process where an organic hydroperoxide charge stock is reacted with an olefin charge stock having about 3-20 carbon atoms in liquid phase with an organic solvent in a reaction zone in the presence of a metallic epoxidation catalyst to form a product olefin epoxide corresponding to the olefin charge stock and a product alcohol corresponding to the hydroperoxide charge, which process is improved in accordance with the present invention as follows:

reacting, in a primary epoxidation reaction zone, an olefin charge stock and organic hydroperoxide in liquid phase with an organic solvent, in the presence of a metallic epoxidation catalyst, under conditions for conversion of 85-95% of the organic hydroperoxide and production of a primary epoxidation reaction product comprising unreacted olefin, olefin oxide, alcohol corresponding to the hydroperoxide, unreacted hydroperoxide, oxidation catalyst, and side reaction products including carboxylic acids;

fractionating, in a primary fractionation zone, the primary epoxidation reaction product into a distillate fraction comprising unreacted olefin and olefin oxide, and into a primary liquid fraction comprising unreacted hydroperoxide, epoxidation catalyst, alcohol and side reaction products including carboxylic acids; reacting, in a secondary reaction zone, primary liquid fraction with excess olefin in a second epoxidation zone under conditions for conversion of 85-95% of the organic hydroperoxide present and for production of a secondary epoxidation reaction product comprising unreacted hydroperoxide, unreacted olefin, olefin oxide, alcohol corresponding to the organic hydroperoxide, epoxidation catalyst, and side reaction products;

fractionating, in a secondary fractionation zone, the secondary epoxidation product into a secondary distillate fraction comprising unreacted olefin and olefin oxide, and into a secondary heavy liquid fraction comprising epoxidation catalyst, alcohol, unreacted hydroperoxide and side reaction products including carboxylic acids; and recovering unreacted olefin and olefin oxide from the primary and secondary distillate fractions.

As desired, the second heavy liquid fraction may be further treated for recovery of alcohol and of the metal values from the epoxidation catalysts.

BRIEF DESCRIPTION OF THE DRAWING

The drawing is a schematic representation of an olefin epoxidation process embodying the present invention.

DETAILED DESCRIPTION OF THE INVENTION AND PREFERRED EMBODIMENTS

In the process of the present invention, olefin reactants may be used which produce an olefin oxide which is lower boiling than, and can be separated from, the organic hydroperoxide reactant. Lower boiling $C_3$-$C_4$ olefins such as propylene, normal butylene, and isobutylene are advantageously epoxidized in the epoxidation reactions of the present invention. Propylene, for manufacture of propylene oxide, is the preferred olefin charge for reaction in the epoxidation reactions disclosed herein. It is, however, contemplated that different olefin reactants, such as propylene and isobutylene, may be reacted separately in the primary and secondary epoxidation reaction zones. For example, propylene in the primary reaction zone and isobutylene in the secondary reaction zone. In such event, separate oxide purification zones may be required for the first and for the second reaction zones. Organic hydroperoxides which may be used in the epoxidation process of the present invention are those capable of epoxidizing the olefin reactants under the disclosed epoxidation reaction conditions such as tertiary butyl hydroperoxide and tertiary amyl hydroperoxide. Tertiary butyl hydroperoxide is preferred as reactant in the epoxidation reactions disclosed herein.

The epoxidation reactions contemplated herein are carried out in the liquid phase with the olefin and hydroperoxide reactants and epoxidation catalyst dissolved in an organic solvent. The solvent may be a non reactive organic liquid in which the reactants and the catalysts are substantially soluble. Preferably, the solvent is the alcohol which corresponds to the organic hydroperoxide used as reactant in the epoxidation reaction. Where tertiary butyl hydroperoxide is the organic hydroperoxide used, then preferably the organic solvent is tertiary butyl alcohol. This is particularly convenient since common industrial processes for manufacture of tertiary butyl hydroperoxide by direct oxidation of isobutane produces a mixture of tertiary butyl hydroperoxide and tertiary butyl alcohol. By varying oxidation conditions, the ratio of tertiary butyl hydroperoxide to tertiary butyl alcohol may be varied to produce a preferred charge stock for the primary epoxidation reaction.

Catalysts used in the epoxidation reactions of the present invention are compounds of metals having high activity for conversion of the hydroperoxide with high selectivity to olefin oxide and alcohol. The most effective catalytic metals are vanadium, tungsten, molybdenum, titanium and selenium. The preferred metal catalyst is molybdenum, and may be present in the epoxidation reaction mixture in an amount equivalent to about 20-1000 ppm based upon the weight of total reactor charge. The catalysts are normally employed as compounds soluble in the epoxidation reaction mixture. These catalysts comprise high molecular weight, highly complex compounds, which, because of their low volatility, are carried through the epoxidation reactions and subsequent fractionations as components of the non-distillate liquid fractions. Many such molybdenum compounds, having high catalytic activity, are known and have been described. For example, see Isaacs U.S. Pat. No. 4,598,057, and also see Marquis, et al, U.S. Pat. No. 4,626,569; 4,650,886; 4,654,427; 4,703,029; and 4,758,681, including catalysts described in the prior art discussed in these patents. The Marquis, et al patents are directed to molybdenum/alkanol and molybdenum/glycol complexes which contain high concentrations of molybdenum and are particularly useful as catalysts in the olefin epoxidation reactions.

The process of the present invention may be understood more readily by reference to the drawing, which is a schematic representation of one preferred embodiment of the invention. As propylene and tertiary butyl hydroperoxide are typical preferred charge stocks to the epoxidation process of the present invention, for illustration purposes, but without intending any limitation on the scope of the invention, the drawing and the improved epoxidation process embodied therein will be described in terms of these reactants with tertiary butyl alcohol as solvent. In the drawing, a solution of tertiary butyl hydroperoxide and tertiary butyl alcohol from line 1 and molybdenum epoxidation catalyst from line 2 are mixed in line 3, and the mixture charged to primary reaction zone 4. Propylene in line 5 is charged to reaction zone 4 also. The propylene and tertiary butyl hydroperoxide are reacted in primary reaction zone 4 under epoxidation conditions, in liquid phase with the tertiary butyl alcohol solvent, in the presence of molybdenum catalyst. The epoxidation reaction in primary reaction zone 4 may be conducted under reaction conditions similar to those disclosed in Marquis, et al. U.S. Pat. No. 4,891,437, which is incorporated herein in its entirety for all purposes.

From lines 1 and 3, the tertiary butyl hydroperoxide is charged to primary reaction zone 4 as at least a 30%, preferably a 40-75%, by weight solution in the tertiary butyl alcohol, sufficient to maintain a primary zone reaction mixture composed of more than 60 wt. polar components (hydroperoxide, alcohol and olefin oxide). Propylene from line 5 is charged to primary reaction zone 4 in an amount sufficient to provide from about 0.5 to about 3.0 moles, preferably 0.9 to about 2.0 moles, of charged olefin per mole of charged hydroperoxide. The epoxidation reaction and primary reaction zone 4 is conducted at a temperature in the range of about 50°-180° C., with a preferred range of between 90°-140° C. An especially preferred range is about 100°-130° C. Pressure is sufficient, in the range of about 200-1000 psig, to maintain the primary zone reaction mixture in the liquid phase.

Molybdenum catalyst from line 2 is provided in an amount sufficient to maintain catalyst concentration in the primary zone reaction mixture in the range of about 50-1000 ppm by weight, calculated as molybdenum, in the total reactor charge. Molybdenum concentration is preferably 200-600 ppm, and most preferably, 250-500 ppm. Advantageously, the catalyst may be a molybdenum/ethylene glycol complex as disclosed in Marquis, et al. U.S. Pat. No. 4,626,596.

In primary reaction zone 4, the reaction is carried out to achieve a hydroperoxide conversion of about 85 to about 95%, for maintaining high selectivity of converted hydroperoxide to olefin oxide and to corresponding alcohol. The use of only a small molar excess of olefin to hydroperoxide and of a more polar reaction mixture contributes to increased selectivities of the reactants.

In primary reaction zone 4, the residence time of reactants may vary considerably from minutes to hours, depending upon other reaction variables such as reaction temperature, ratio of reactants, reactant concentration in the reaction mixture, catalyst concentration and catalyst activity. Generally, reaction times will run between 30 minutes and 4 hours, with 0.5 to 2.0 hours being typical.

In primary reaction zone 4, the epoxidation reaction is preferably staged, with a first stage carried for a time at a selected reaction temperature and a second stage (or subsequent stages) carried out at equal or higher temperatures. For example, the epoxidation reaction may be conducted for 1 hour at 110°-120° C., and for a second hour at 120°-130° C. For continuous processes, a series of reactors help to achieve the objective of high selectivity to olefin oxide and alcohol of converted hydroperoxide. The use of a series of reactors in primary reaction zone 4 makes it possible to stage the addition of olefin reactant and thereby increase reaction mixture polarity and, concomitantly, decrease formation of olefin side reaction products, i.e., hydrocarbon dimers (hexenes) in the case of propylene reactant.

In primary reaction zone 4, the reactor stages may be two temperature stages in the same reactor vessel, two or more back mixed reactors, such as continuously stirred tank reactors (CSTR's) in series, or, preferably, one or more back mixed reactors followed by one or more plug flow reactors (PFR's). In back mixed reactors, such as CSTR's, the concentration of reactant olefin and hydroperoxide is low, which helps retard side reactions whose rate depends on reactant concentration. On the other hand, in non-back mixed PFR reactors, the reaction products are kept away from fresh reactants, thus reducing the reactant side reactions catalyzed by acid by-products.

Under conditions in epoxidation reaction zones, organic hydroperoxides (tertiary butyl hydroperoxide) are subject to thermal or catalytic decomposition leading to formation of unwanted side reaction products, including $C_1$-$C_4$ carboxylic acids. Such decomposition and formation of side reaction products are particularly troublesome at temperatures as the range of 100°-180° C., particularly above 130° C. which are commonly used in epoxidation reactions of the prior art.

In the drawing, the epoxidation reaction in primary reaction zone 4 is undertaken under conditions including only a small molar excess of olefin to hydroperoxide, a reaction mixture containing at least 60% polar compounds and lower reaction temperatures, preferably 100°-130° C., for increasing selectivity of converted tertiary butyl hydroperoxide to formation of propylene oxide and tertiary butyl alcohol and for inhibiting propylene dimerization or reaction with tertiary butyl hydroperoxide in etherification or esterification reactions. Preferably, the epoxidation reaction in the primary epoxidation zone 4 is carried out to achieve hydroperoxide conversions range of about 85-95%. Thus, 5 to 15 wt. % of the hydroperoxide will remain unconverted in the primary zone reaction mixture.

The rate of hydroperoxide conversion, under epoxidation reaction conditions, is directly proportional to both hydroperoxide and olefin concentration in the reaction mixtures. In primary reaction zone 4, tertiary butyl hydroperoxide concentration and propylene concentration in the combined charge stock are quite high (approximately 20-50 wt. % hydroperoxide and 20-30 wt. % propylene within the preferred ranges). Epoxidation reactions are highly exothermic and reaction of hydroperoxide and olefin at such high initial concentrations will rapidly generate substantial heat which must be removed to control the reaction temperature within a desired range. As discussed above with reference to primary reaction zone 4, back mixed reactors may be used to mix incoming charge with existing reaction mixture, thus maintaining a moderate concentration of reactants in the reaction zone, and concomitantly maintaining a moderate reaction rate.

In the drawing, primary epoxidation reaction product is withdrawn from the primary reaction zone 4 by way of discharge line 6. The primary epoxidation reaction product comprises unreacted propylene, unreacted tertiary butyl hydroperoxide, propylene oxide, tertiary butyl alcohol, molybdenum catalyst and side reaction products such as oxygenated compounds, including $C_1$-$C_4$ carboxylic acids, and hydrocarbons containing six or more carbon atoms. Primary oxidation reaction zone product from line 6 is charged to primary distillation zone 7 where the reaction product is fractionated into a primary overhead vapor fraction comprising propylene, propane and propylene oxide, and into a primary heavy liquid fraction comprising tertiary butyl alcohol, unreacted tertiary butyl hydroperoxide, molybdenum catalyst and higher boiling side reaction products including carboxylic acids. The primary vapor fraction is withdrawn from primary distillation zone 7 via line 8 and is charged into propylene oxide distillation zone 9 as will be described herein below.

In the drawing, primary liquid fraction, withdrawn from primary distillation zone 7 via line 10 comprises about 5-10 wt. % tertiary butyl hydroperoxide, 80-90 wt. % tertiary butyl alcohol, molybdenum catalyst, and 5-10% side reaction products, including carboxylic acids which catalyze side reactions which destroy olefin and hydroperoxide reactants and olefin oxide product. Primary liquid fraction from line 10 and propylene from line 12 are charged to secondary reaction zone 11 for conversion of hydroperoxide and production of olefin oxide and alcohol corresponding to the hydroperoxide.

In second reaction zone 11, hydroperoxide concentration in primary liquid fraction from line 10 is low (5-10 wt. %). Consequently, steps to moderate the reaction rate, in secondary reaction zone 11 are not required. Preferably, steps to increase the reaction rate, such as use of PFR reactors and increasing ratio of propylene reactant to hydroperoxide, are employed. Reducing the residence time in secondary reaction zone 11 during which propylene and hydroperoxide reactants and propylene oxide product are in contact with the carboxylic acid side reaction products will decrease the deleterious side reactions catalyzed by these acids.

In the drawing, primary liquid fraction from line 10 is highly polar, containing 5-10 wt. % tertiary butyl hydroperoxide and 80-90 wt. % tertiary butyl alcohol, with the remainder being molybdenum catalyst and side reaction products (5-10 wt. %). Thus, a substantial molar excess of propylene with respect to hydroperoxide may be charged to secondary reaction zone 11 while continuing to maintain 60% or more polar compounds (hydroperoxide, alcohol, propylene oxide) in the reaction mixture. A molar ratio of propylene to hydroperoxide within the range of about 5:1 to about 10:1 may be charged while maintaining an overall concentration of polar compounds in the secondary reaction mixture above about 60%. The more polar reaction mixture tends to stabilize the tertiary butyl hydroperoxide and render the molybdenum catalyst more active, thus improving hydroperoxide conversion and selectivity. Increased propylene concentration increase the rate of the epoxidation reaction allowing decreased residence time in secondary reaction zone 11.

In the drawing, reaction temperatures in the secondary epoxidation reaction zone 11 may be in the range of about 50°-180° C. Lower temperatures improve selectivity of converted hydroperoxide to desired olefin oxide and alcohol products and reduce the rate of undesired side reactions, such as olefin dimerization, but also result in reduced reaction rates. Higher temperatures increase hydroperoxide conversion and olefin oxide production rates, but also increase the rates of undesirable side reactions which decrease selectivity of hydroperoxide conversion to desired products. Preferably, reaction temperatures in secondary epoxidation reaction zone 11 are maintained in the range of about 110°-130° C. for maintaining a high rate of reaction and high selectivity of converted hydroperoxide to olefin oxide and alcohol, while controlling destructive side reactions to a low level.

Pressure in secondary reaction zone 11 is maintained in the range of about 200–1000 psig, sufficient to maintain the secondary reaction mixture in the liquid phase.

In the drawing, residence time of secondary reaction mixture in secondary reaction zone 11 is preferably in the range of about 30 minutes to 2 hours, sufficient, at the selected reaction conditions, to obtain conversion of about 85–95 wt. % of the hydroperoxide charge. Hydroperoxide conversion above about 95% in each of the primary reaction zone 4 and secondary reaction zone 11 is neither desirable nor necessary. For example, if hydroperoxide conversion is 90% in primary reaction zone 4, then only 10% of the hydroperoxide charge enters secondary reaction zone 11. If 90% of that 10% hydroperoxide is converted in secondary reaction zone 11, then overall hydroperoxide conversion for both reaction zones is 99%. No advantage is gained by increasing hydroperoxide conversion much above 99%, while on the other hand limiting hydroperoxide conversion to about 90% in the reaction zones substantially reduces the rate of deleterious side reactions.

From secondary reaction zone 11 a secondary epoxidation reaction product comprising unreacted propylene, unreacted hydroperoxide, tertiary butyl alcohol, propylene oxide, side reaction products, and molybdenum catalysts is withdrawn via line 22 and charged to secondary product distillation zone 13. In secondary product distillation zone 13 the secondary reaction product is separated into a secondary distillate fraction comprising unreacted propylene, propane and propylene oxide, and a secondary liquid fraction comprising tertiary butyl alcohol, unreacted tertiary butyl hydroperoxide, molybdenum catalyst and side reaction products. The secondary liquid fraction is withdrawn from product distillation zone 13 via line 14 and is passed to further treatment (not shown) as desired for recovery or disposal of molybdenum values.

Secondary distillate fraction is withdrawn from secondary distillation zone 13 via line 15 and is charged to propylene oxide distillation zone 9. As described above, primary distillate fraction from primary product distillation zone 7 is also charged via line 8 to propylene oxide distillation zone 9. In propylene oxide distillation zone 9 the primary distillate and secondary distillate are fractionated into a propylene oxide fraction, and an overhead fraction comprising propane and propylene. The propylene oxide fraction is withdrawn from propylene oxide distillation zone 9 via line 17 for further treatment (not shown) to produce a commercial propylene oxide product. Overhead fraction from propylene oxide distillation zone 9 is withdrawn via line 18 to propane splitter 19. In propane splitter 19 the overhead fraction charged is fractionally distilled into a propylene fraction and a propane fraction. The propane fraction is withdrawn from propane splitter 19 via line 20 for disposal (not shown). The propylene fraction withdrawn from propylene splitter 19 via line 21 may be recycled as propylene charge stock to primary reaction zone 4 and/or secondary reaction zone 11.

EXAMPLES

The process of the present invention is illustrated by the following examples which are given by way of illustration only and not as limitation on the scope of this invention which is defined in the appended claims.

EXAMPLE I

All experiments described herein were conducted employing bench scale reactors comprising a continuously stirred tank reactor (CSTR) and two plug flow tubular reactors (PFR). In the experiments (6685-30 & 6685-55) illustrating the process of the present invention, the primary epoxidation reaction zone comprised the CSTR reactor followed by one PFR reactor, and the secondary epoxidation reaction zone comprised the other PFR reactor. In the comparative experiments (6305-99 & 6362-12), embodying processes of the prior art where only a primary reaction zone is employed, the primary reaction zone comprised the CSTR reactor followed by the two PFR reactors all arranged in series. By arranging the experiments in this manner, the total reactor volume for each experiment, whether of an inventive or a comparative process, was identical with reactor volumes in the other experiments. Consequently, results obtained in the experiments may be compared for purposes of determining the advantages of the process of the present invention over the comparative processes of the prior art. Two inventive experiments, 6685-30 and 6685-55 were performed. In inventive experiment 6685-30 four pounds per hour of a solution comprising 55 wt % tertiary butyl hydroperoxide and 45 wt % tertiary butyl alcohol, 1.75 pounds per hour propylene, and about 5 gm/hour of a molybdenum-ethylene glycol complex catalyst comprising about 13 wt % molybdenum were charged to the CSTR reactor. The CSTR reactor was maintained at a temperature of 120° C., and a pressure of about 500 psig sufficient to maintain the reaction mixture in the liquid phase. From the CSTR reactor the reaction mixture flowed into the first PFR reactor which was maintained at 130° C. Residence time of reactants in the CSTR and first PFR which comprised the primary reaction zone, was about 0.8 hours.

Reaction product from the first PFR reactor was withdrawn and analyzed, showing a tertiary butyl hydroperoxide conversion of 88%. This reaction product was charged to a fractional distillation column where it was separated into an overhead fraction comprising propylene and propylene oxide and a bottoms fraction comprising the tertiary butyl alcohol, unreacted tertiary butyl hydroperoxide, molybdenum catalyst and side reaction products, including carboxylic acids which catalyze further side reactions. The bottoms fraction from the primary fractionation column, containing about 7 wt % tertiary butyl hydroperoxide, was charged to the second PFR, which comprised the secondary reaction zone, at a rate of 3.6 pounds per hour along with one pound per hour of propylene. Fractionater bottoms and propylene formed the charge to the second reactor and had an initial molar ratio of propylene to tertiary butyl hydroperoxide of about 8.5:1. In the secondary reaction zone, the reaction mixture was maintained in the liquid phase at a pressure of about 500 psig and a reaction temperature of about 130° C. for a residence time of about 0.8 hours. Under such conditions, about 91.7% of tertiary butyl hydroperoxide charged to the second reactor was converted. Operating conditions for the experiment 6685-30 are shown in Table I. Hydroperoxide conversion and selectivities to production of propylene oxide and tertiary butyl alcohol are shown in Table II. Example 6685-55, which also embodied the process of the present invention, was operated under substantially the same conditions as experiment 6685-30, except temperature was increased to 130° C. Operating conditions for this experiment tions for 6362-12 are shown in Table I and conversion and yields are shown in Table II.

TABLE I

EPOXIDATION OF PROPYLENE WITH TERTIARY BUTYL HYDROPEROXIDE REACTION CONDITIONS

PRIMARY REACTION ZONE

| Experiment No. | TBHP feed rate #/Hr. | Propylene feed rate #/Hr. | TBHP/TBA Ratio wt. | Propylene/TBHP Ratio molar | Moly. Cat. Conc. ppm-wt. | CSTR Temp C. | 1st. PFR Temp. C. | 2nd. PFR Temp. C. | Res. Hrs. |
|---|---|---|---|---|---|---|---|---|---|
| 6685-30 | 2.2 | 1.63 | 55:45 | 1.6:1 | 262 | 120 | 130 | — | 0.8 |
| 6685-55 | 2.2 | 1.63 | | 1.6:1 | 255 | 130 | 130 | — | 0.8 |
| 6305-99 | 2.2 | 1.50 | | 1.5:1 | 245 | 120 | 130 | 130 | 0.8 |
| 6362-12 | 2.2 | 1.39 | | 1.5:1 | N/A | 120 | 130 | 130 | 0.8 |

N/A Not Available

SECONDARY REACTION ZONE

| Experiment No. | TBHP feed rate #/Hr. | Propylene feed rate #/Hr. | Propylene/TBHP Ratio molar | TBHP* Conc. wt. % | Moly. Cat. Conc. ppm-wt. | PFR Temp. C. | Res. Time Hrs |
|---|---|---|---|---|---|---|---|
| 6685-55 | 0.254 | 1.0 | 8.5:1 | 7.2 | 436 | 130 | 0.8 |
| 6685-55 | 0.24 | 1.0 | 8.9:1 | 6.7 | 385 | 130 | 0.8 |

*TBHP % in Reactor Feed
N/A-"Not Applicable"

TABLE II

EPOXIDATION OF PROPYLENE WITH TERTIARY BUTYL HYDROPEROXIDE YIELDS

| Experiment No. | TBHP Prim. Rx. % Conv. | TBHP Sec. Rx. % Conv. | TBHP Overall % Conv. | TBHP/PO Selectivity % | TBHP/TBA Selectivity % | PO/TBHP Yield mol/mol | TBA/TBHP Yield mol/mol |
|---|---|---|---|---|---|---|---|
| 6685-30 | 88.5 | 91.7 | 99 | 93.5 | 96.1 | 0.93:1 | 0.95:1 |
| 6685-55 | | | 99 | 93.3 | 96.5 | 0.92:1 | 0.96: |
| 6305-99 | 97.3 | | 97.3 | 90.4 | 93.9 | 0.88:1 | 0.91:1 |
| 6362-12 | 98.4 | | 98.4 | 88.3 | 93.1 | 0.87:1 | 0.92:1 |

TBHP - tertiary butyl hydroperoxide
TBA - tertiary butyl alcohol
PO - propylene oxide 6685-55 are shown in Table I and conversion and yield for the reaction are shown in Table II.

Experiment 6305-99 and 6362-12 are comparative examples employing a process of the prior art. In these experiments only a primary reaction zone was used. This primary reaction zone comprised the CSTR reactor and the two PFR reactors employed in the inventive experiments 6685-30 & 6685-55 described above. However, in these comparative experiments, the CSTR reactor and the two PFR reactors were arranged in series in a single primary reaction zone. In operation, about 4 pounds per hour of the solution comprising about 55 wt % tertiary butyl hydroperoxide and 45 wt % tertiary butyl alcohol was charged along with about 1.75 pounds per hour of propylene and about 5 g/hr of molybdenum-ethylene glycol complex catalyst to the CSTR reactor. The CSTR was maintained at a temperature of about 120° C. and a pressure of about 500 psig, sufficient to maintain the reaction mixture in the liquid phase. Reaction mixture from the CSTR reactor flowed into the first PFR reactor which was maintained at 130° C. and from there into the second PFR reactor which was likewise maintained at 130° C. Residence time in the primary reaction zone for this comparative experiment was about 1.6 hours.

Reaction product from the last PFR in the primary reaction zone was withdrawn and analyzed showing a tertiary butyl hydroperoxide conversion of 97.3%. Operating conditions for experiment 6305-99 are shown in Table I, and conversion and yields from the reaction are shown in Table II. Experiment 6362-12 was substantially a duplicate of example 6305-99. Operating conditions for 6362-12 are shown in Table I and conversion and yields are shown in Table II.

Examining the results for both inventive and comparative experiments reported in Table II, it can be seen that the process of the present invention (experiments 6685-30 & 6685-55) clearly exhibits advantages over the comparative process (experiments 6362-12 & 6305-99) of the prior art. That is, in the inventive experiments 6685-30 and 6685-55 the overall tertiary butyl hydroperoxide conversion is 99% while the tertiary butyl hydroperoxide conversion for the two comparative experiments 6362-12 & 6305-99 are 97.3% and 98.4% respectively. Thus, tertiary butyl hydroperoxide conversion is somewhat improved and selectivity of converted tertiary butyl hydroperoxide to desired propylene oxide and tertiary butyl alcohol products is substantially improved in the process of the present invention as compared to the process of the prior art. For example, comparing inventive experiment 6685-30 with comparative experiments 6305-99 and 6362-12, the yield of propylene oxide per mole of tertiary butyl hydroperoxide is 0.93:1 compared to 0.88:1. This is 5% improvement in propylene oxide yield. Similarly, the yield of tertiary butyl alcohol per mole of tertiary butyl hydroperoxide is 0.95:1 compared to 0.91:1, for a 4% improvement in yield.

While the invention has been illustrated and described in detail in the drawing and forgoing description, the same are to be considered illustrative only and not limiting in character, and that many changes and modifications may be made by those skilled in the art without departing from the spirit and scope of the invention which is defined only by the appended claims.

We claim:

1. In an epoxidation process wherein olefin and an organic hydroperoxide are reacted in liquid phase with a polar organic solvent in the presence of a soluble epoxidation catalyst for production of olefin oxides and alcohol corresponding to the organic hydroperoxide, the improvement which comprises:
   a) charging organic hydroperoxide, polar organic solvent, soluble epoxidation catalyst and a first olefin to a primary epoxidation reaction zone under primary zone epoxidation reaction conditions, forming a primary zone reaction mixture;
   b) maintaining the primary zone epoxidation reaction conditions, including a primary zone reaction pressure sufficient to maintain the primary zone reaction mixture in liquid phase, for conversion from about 85% to about 95% of the organic hydroperoxide;
   c) recovering, from the primary epoxidation reaction zone, a primary zone reaction product comprising unreacted first olefin, first olefin oxide, unreacted organic hydroperoxide, alcohol corresponding to organic hydroperoxide, polar organic solvent, epoxidation catalyst and side reaction products;
   d) fractionating, in a primary fractionation zone, the primary zone reaction product into a primary distillate fraction comprising unreacted first olefin and first olefin oxide, and into a primary liquid fraction comprising alcohol corresponding to the organic hydroperoxide, polar organic solvent, unreacted organic hydroperoxide, epoxidation catalyst and side reaction products;
   e) charging primary liquid fraction and a second olefin to a secondary epoxidation reaction zone under secondary zone epoxidation reaction conditions, forming a secondary zone reaction mixture;
   f) maintaining secondary zone epoxidation reaction conditions, including a secondary zone reaction pressure sufficient to maintain the secondary zone reaction mixture in liquid phase, for conversion from about 85% to about 95% of the organic hydroperoxide in the primary liquid fraction;
   g) recovering, from the secondary epoxidation reaction zone, a secondary zone reaction product comprising unreacted second olefin, unreacted organic hydroperoxide, alcohol corresponding to the organic hydroperoxide, polar organic solvent, second olefin oxide, epoxidation catalyst and side reaction products;
   h) recovering first olefin oxide from the primary distillate fraction; and
   i) recovering second olefin oxide and alcohol corresponding to the organic hydroperoxide from the secondary zone reaction product.

2. The process of claim 1:
   wherein the first and second olefins are selected from the group consisting of propylene, n-butylene and isobutylene;
   wherein the organic hydroperoxide is selected from the group consisting of tertiary butyl hydroperoxide and tertiary amyl hydroperoxide; and
   wherein the epoxidation catalyst is a molybdenum compound soluble in the primary zone reaction mixture and in the secondary zone reaction mixture.

3. The process of claim 2, including:
   a) charging organic hydroperoxide and polar organic solvent to the primary epoxidation reaction zone in a weight ratio in the range from about 30:70 to about 75:25 respectively;
   b) charging first olefin to the primary epoxidation reaction zone in a molar ratio of first olefin to organic hydroperoxide in the range from about 0.9:1 to about 3:1 respectively;
   c) maintaining the primary epoxidation reaction zone at a primary zone reaction temperature in the range from about 100° C. to about 140° C., at a primary zone reaction pressure in the range from about 200 psig to about 1000 psig sufficient to maintain the primary zone reaction mixture in liquid phase, and at a primary epoxidation reaction zone residence time in the range from about 30 minutes to about 2 hours;
   d) charging second olefin and primary liquid fraction, in amounts sufficient to maintain a molar ratio of second olefin to organic hydroperoxide in the range from about 5:1 to about 10:1, respectively, to the secondary epoxidation reaction zone
   e) maintaining the secondary epoxidation reaction zone at a secondary zone reaction temperature in the range from about 100° C. to about 140° C., at a secondary zone reaction pressure in the range from about 200 psig to about 1000 psig sufficient to maintain the secondary zone reaction mixture in liquid phase, and at a secondary epoxidation reaction zone residence time in the range from about 30 minutes to about 2 hours.

4. The process of claim 3, wherein the polar solvent is alcohol corresponding to the organic hydroperoxide, and wherein the first olefin and the second olefin are the same.

5. In an epoxidation process wherein propylene and tertiary butyl hydroperoxide are reacted in liquid phase with tertiary butyl alcohol solvent in the presence of a soluble molybdenum catalyst, for production of propylene oxide product and tertiary butyl alcohol product, the improvement which comprises:
   a) charging to a primary epoxidation reaction zone, under primary zone epoxidation reaction conditions, tertiary butyl hydroperoxide, tertiary butyl alcohol, a first propylene stream, and soluble molybdenum catalyst in a tertiary butyl hydroperoxide to tertiary butyl alcohol weight ratio from about 30:70 to about 75:25, respectively, in a propylene to tertiary butyl hydroperoxide molar ratio from about 0.9:1 to about 3:1, respectively, and in an amount of molybdenum catalyst equivalent to about 50 to about 1000 ppm molybdenum based upon total charge to the primary epoxidation reaction zone, forming a primary zone reaction mixture having a polar compound concentration of at least 60% by weight;
   b) maintaining the primary epoxidation reaction zone under primary zone epoxidation reaction conditions, including a primary zone reaction pressure sufficient to maintain the primary zone reaction mixture in liquid phase, for conversion of about 85% to about 95% of the charged tertiary butyl hydroperoxide;
   c) producing a primary zone reaction product comprising unreacted first propylene, propylene oxide, tertiary butyl alcohol, unreacted tertiary butyl hydroperoxide, molybdenum catalyst and side reaction products;
   d) fractionating, in a primary fractionation zone, the primary zone reaction product into a primary distillate fraction comprising unreacted first propylene and propylene oxide, and into a primary liquid fraction comprising tertiary butyl alcohol, unreacted tertiary butyl hydroperoxide, molybdenum catalyst and side reaction products;

e) charging primary liquid fraction and a second propylene stream, in amounts for providing a molar ratio of propylene to tertiary butyl hydroperoxide of about 5:1 to about 10:1, respectively, to a secondary epoxidation reaction zone under secondary zone epoxidation reaction conditions, forming a secondary zone reaction mixture;

f) maintaining the secondary epoxidation reaction zone under secondary zone epoxidation reaction conditions, including a secondary zone reaction pressure sufficient to maintain secondary zone reaction mixture in liquid phase, for conversion of about 85% to about 95% of tertiary butyl hydroperoxide from the charged primary liquid fraction;

g) producing a secondary zone reaction product comprising unreacted tertiary butyl hydroperoxide, unreacted second propylene, propylene oxide, tertiary butyl alcohol, molybdenum catalyst and side reaction products;

h) recovering propylene oxide product from the primary distillate fraction; and i) recovering propylene oxide product and tertiary butyl alcohol product from the secondary zone reaction product.

6. The process of claim 5 including:
a) maintaining a primary zone reaction temperature in the range from about 100° C. to about 140° C.;
b) charging tertiary butyl hydroperoxide and tertiary butyl alcohol in a weight ratio in the range from about 45:55 to about 75:25, respectively, to the primary epoxidation reaction zone; and
c) charging first propylene stream in an amount to provide propylene and tertiary butyl hydroperoxide in a molar ratio in the range from about 0.9:1 to about 2:1, respectively, to the primary epoxidation reaction zone.

7. The process of claim 6, including:
maintaining the secondary zone reaction temperature in the range from about 100° C. to about 140° C.

8. The process of claim 7, including:
maintaining the primary zone reaction temperature in the range from about 100° C. to about 130° C.; and
maintaining the secondary zone reaction temperature in the range from about 120° C. to about 140° C.

9. The process of claim 8, including:
staging the primary zone reaction temperature within a range from about 100° C. to about 120° C. during a first reaction period and within a range from about 120° C. to about 130° C. during a second reaction period.

* * * * *